United States Patent
Carmichael et al.

(10) Patent No.: US 9,044,622 B2
(45) Date of Patent: Jun. 2, 2015

(54) INVERSE EMULSIONS COMPRISING AN ALKOXYLATED ESTER OIL

(75) Inventors: Kim Moira Carmichael, Merseyside (GB); Adam John Limer, Merseyside (GB); Patrick James Colver, Warrington (GB); Surinder Pall Chahal, Warrington (GB)

(73) Assignee: Croda International PLC, Goole, North Humberside (GB)

( * ) Notice: Subject to any disclaimer, the term of this patent is extended or adjusted under 35 U.S.C. 154(b) by 0 days.

(21) Appl. No.: 13/515,197

(22) PCT Filed: Dec. 22, 2010

(86) PCT No.: PCT/GB2010/002307
§ 371 (c)(1),
(2), (4) Date: Jun. 11, 2012

(87) PCT Pub. No.: WO2011/077083
PCT Pub. Date: Jun. 30, 2011

(65) Prior Publication Data
US 2012/0288464 A1    Nov. 15, 2012

(30) Foreign Application Priority Data

Dec. 24, 2009 (GB) .................................. 0922624.2

(51) Int. Cl.
*A61Q 5/00* (2006.01)
*A61K 47/14* (2006.01)
*A61Q 19/00* (2006.01)
*A61K 8/06* (2006.01)
*A61K 8/39* (2006.01)
*A61K 8/81* (2006.01)
*C08F 2/32* (2006.01)

(52) U.S. Cl.
CPC . *A61Q 19/00* (2013.01); *A61K 8/06* (2013.01); *A61K 8/062* (2013.01); *A61K 8/064* (2013.01); *A61K 8/39* (2013.01); *A61K 8/8158* (2013.01); *A61K 2800/48* (2013.01); *A61Q 5/00* (2013.01); *C08F 2/32* (2013.01)

(58) Field of Classification Search
None
See application file for complete search history.

(56) References Cited

U.S. PATENT DOCUMENTS

| | | | |
|---|---|---|---|
| 3,734,873 A | 5/1973 | Anderson et al. | |
| 4,764,574 A | 8/1988 | Clark | |
| 5,925,714 A | 7/1999 | Larson et al. | |
| 6,476,254 B1 * | 11/2002 | Pereira et al. | 560/198 |
| 2006/0269490 A1 * | 11/2006 | Braun et al. | 424/59 |

FOREIGN PATENT DOCUMENTS

| | | |
|---|---|---|
| JP | S63-208508 | 8/1988 |
| JP | 2003-523928 | 8/2003 |
| JP | 2005-506347 | 3/2005 |
| WO | WO 00/19972 | 4/2000 |
| WO | WO 03/032919 | 4/2003 |

OTHER PUBLICATIONS

International Search Report dated Jun. 7, 2011 for PCT/GB2010/002307.
Office Action, dated Oct. 7, 2014, from corresponding Japanese Patent Application No. 2014-545429.

* cited by examiner

*Primary Examiner* — Michael B Pallay
(74) *Attorney, Agent, or Firm* — Jones Day

(57) ABSTRACT

Inverse emulsions made by inverse emulsion polymerization have a disperse aqueous phase comprising a solution or dispersion of at least one water soluble polymer, particularly a polymer that forms a viscous solution or dispersion in water, and a continuous oil phase which is or includes an ester oil including an alkoxylated alcohol group. The inclusion of ester oil including an alkoxylated alcohol group provides these oils in emulsions, particularly personal care emulsions made by inversion of the inverse emulsions on dilution with water.

4 Claims, No Drawings

INVERSE EMULSIONS COMPRISING AN ALKOXYLATED ESTER OIL

CROSS REFERENCE TO RELATED APPLICATION

This application is the National Phase application of International Application No. PCT/GB2010/002307, filed Dec. 22, 2010, which designates the United States and was published in English. This application, in its entirety, is incorporated herein by reference.

This invention relates to inverse (water in oil) emulsions of aqueous solutions or dispersions of water soluble polymers in oils which are or include emollient oils particularly ester oils based on alkoxylated alcohol moieties, and in particular to making such emulsions by reverse phase or inverse emulsion polymerisation, and to the use of such emulsions in personal care products.

Polymers used for rheology modification, particularly thickening, of aqueous systems often tend to form very viscous solutions or dispersions, which can be seen as highly viscous lumps which are difficult to disperse, particularly if the, usually solid, polymer is directly mixed with water. One way around this is to provide the polymer well dispersed in a non-aqueous medium before mixing this with the water. A particularly convenient way of doing this is to make the thickening polymer by an inverse emulsion polymerisation process, and then inverting the inverse emulsion by diluting it into water. Inverse emulsion polymerisation methods are described in U.S. Pat. No. 2,982,749, U.S. Pat. No. 3,284,393 and U.S. Pat. No. 4,506,062. Subsequently the advantages of inversion on dilution were appreciated and this became a normal procedure, notably for polyacrylamide used in water purification as described in WO98/09998 A and for making homo-/co-polymers of water soluble monomers as described in GB 1384470 A.

Such polymers are commonly used as thickeners in the personal care industry, where ionic and non-ionic hydrophilic monomers are frequently used, for example acrylates and methacrylates, particularly as free acids or salts with alkali metals, ammonia or amines. When used in the form of inverse emulsions, they commonly use mineral oil as the continuous phase but other oils have been suggested e.g. silicones (WO 2002/044228 A), di- and tri-glycerides, esters (US 2002/0032243 A) and, for making acrylamides, ester based, particularly vegetable, oils (WO 98/09998 A). However, for personal care use, such products and methods commonly use oil phases that are not especially desirable in the intended personal care products.

Thickeners are widely used in personal care products, frequently formulated in combination with components such as surfactants, fragrances, preservatives and antimicrobials. An important component for topical skincare applications is a skin conditioning agent or emollient. Typically emollients include fatty acid esters of which a very wide range are known for use as emollients. Esters of alkoxylated alcohols and carboxylic acids are suggested as emollients in personal care formulations in U.S. Pat. No. 5,693,316, U.S. Pat. No. 5,455,025 and U.S. Pat. No. 6,476,254.

This invention is based on our finding that the use of alkoxylated esters of carboxylic acids can give inverse emulsions containing water soluble polymers, particularly such polymers that act as thickeners in aqueous solution, with advantageous properties, notably that it is possible to get improved viscosity build compared to conventional inverse emulsion thickeners, and benefits arising from the emolliency properties of the alkoxylated esters.

This approach simplifies personal care product formulation by delivering such enhanced emollients in the oil phase of the inverse emulsion which carries the rheology modifying, usually thickening, polymer. This may provide both sensory and rheological benefits, in that it may provide enhanced skin feel over standard mineral oil inverse emulsions as evidenced by improved break/yield points. Further alkoxylated esters can provide significant self emulsification and this can be used to reduce the overall level of emulsifier surfactants needed in the end products.

According to a first aspect of the present invention there is provided an inverse (water in oil) emulsion made by inverse emulsion polymerisation having a disperse aqueous phase comprising a solution or dispersion of at least one water soluble polymer, particularly a polymer that forms a viscous solution or dispersion in water, and a continuous oil phase which is or includes an ester oil including an alkoxylated alcohol group.

The term "water soluble polymer" is understood to refer to polymers that form a solution in water that is substantially free of insoluble polymer particles. In addition, the term also includes embodiments in which the polymer is water-swellable.

According to a second aspect of the present invention there is provided a method of making inverse emulsion having a dispersed aqueous phase, said emulsion comprising:
i) a solution or dispersion of at least one water soluble polymer, particularly a polymer that forms a viscous solution or dispersion in water; and
ii) a continuous oil phase which is or includes an ester oil including an alkoxylated alcohol group,
wherein said method comprises
   a) dispersing in an oil phase an aqueous solution of monomers, said monomers being polymerisable to form a water soluble or dispersible polymer, said oil phase comprising or consisting of at least one ester oil having an alkoxylated alcohol group; and
   b) polymerising said monomers to form a colloidal suspension of particles, of a solution or dispersion of the resulting polymer in water, in the oil.

According to a third aspect of the present invention there is provided an alternative method of making an inverse emulsion having a dispersed aqueous phase, said emulsion comprising:
i) a solution or dispersion of at least one water soluble polymer, particularly a polymer that forms a viscous solution or dispersion in water; and
ii) a continuous oil phase which is or includes an ester oil including an alkoxylated alcohol group,
wherein said method comprises
   a) dispersing in an oil phase an aqueous solution of monomers, said monomers being polymerisable to form a water soluble or dispersible polymer;
   b) polymerising said monomers to form a colloidal suspension of particles, of a solution or dispersion of the resulting polymer in water, in the oil; and
   c) subsequently including in the emulsion at least one ester oil comprising an alkoxylated alcohol group.

In the method of the third aspect the ester oil including an alkoxylated alcohol group may be included in the emulsion:
i) by addition to a preformed emulsion, where the oil in which the emulsion was made is compatible with the downstream use of the emulsion; or
ii) by partial or complete replacement of the oil in which the emulsion was made by the at least one ester oil including an alkoxylated alcohol group.

As an alternative to the emulsion polymerisation method as described in the second and third aspect, the inverse emulsion may be made by micro dispersion polymerisation (also known as miniemulsion polymerisation) in which dispersed droplets of monomer are formed by homogonisation of the aqueous and oil phases, and the monomer is polymerised when in the form or the droplets to provide a colloidal suspension of particles. In this alternative method of making the inverse emulsion, all other features would be as described with reference to the methods of the second or third aspects.

The particular emollient oils used in the inverse emulsions of the invention are esters including alkoxylated alcohol groups. Desirable such esters may be selected from the following, either alone or in any combination:

i esters of long chain fatty acids and alkoxylated fatty aliphatic alcohols, in particular of the formula (I):

wherein
$R^1$ is a $C_7$ to $C_{23}$, especially a $C_9$ to $C_{17}$, hydrocarbyl, particularly alkyl or alkenyl, group; each group $AO^1$ is independently an alkyleneoxy group, particularly an ethyleneoxy or propyleneoxy group;
n1 is from 1 to 15, preferably 1 to 10, particularly 1 to 5;
$R^2$ is a fatty aliphatic, especially a $C_8$ to $C_{20}$ aliphatic group, and particularly an alkyl, alkenyl or alkynyl group;

ii diesters and/or triesters of aliphatic and/or aromatic dicarboxylic and/or tricarboxylic acids and fatty alkoxylated alcohols, in particular of the formula (II):

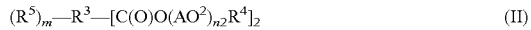

wherein
$R^3$ is a $C_2$ to $C_{10}$ hydrocarbyl group;
$R^4$ is a fatty hydrocarbyl, particularly an alkyl, alkenyl or alkynyl group;
$AO^2$ is an alkyleneoxy group, particularly an ethyleneoxy or propyleneoxy group;
n2 is from 1 to 15, preferably 1 to 10, particularly 1 to 5;
$R^5$ is a group of the formula $R^6O(O)C$— where $R^6$ is selected from H, a salt forming moiety, particularly an alkali metal, ammonium or an amine, or a group $(AO^2)_{n2}R^2$ where $AO^2$, n2 and $R^2$ are as defined above; and
m is equal to either 0 or 1;

Particular desirable esters are citric acid esters of the general formula (IIa):

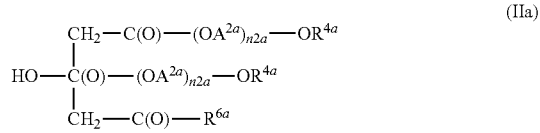

wherein;
each $R^{4a}$ is independently a group $R^4$ as defined in formula (II);
each $OA^{2a}$ is independently a group $AO^2$ as defined in formula (II);
each n2a is independently is from 1 to 15, usually 1 to 10, particularly 1 to 5; and
$R^{6a}$ is selected from H or a group $(AO^{2a})_{n2a}R^{2a}$ where $AO^{2a}$, n2a and $R^{2a}$ are as defined above.

Further desirable esters are dicarboxylic acid esters of the general formula (IIb):

wherein
each $R^{4b}$ is independently a group $R^4$ as defined in formula (II)
each $OA^{2b}$ is independently a group $AO^2$ as defined in formula (II);
each n2b is independently from 1 to 15, usually 1 to 10, particularly 1 to 5; and
each $R^7$ is selected from H, $C_1$ to $C_{30}$ alkyl, or $C_2$ to $C_{30}$ alkenyl group, or together the two groups $R^7$ represent a direct bond between the carbon atoms to which they are attached.

iii esters of fatty carboxylic acids and polyalkoxylates of aromatic alcohols, in particular of the formula (III):

wherein
$R^9$ is a group comprising an aromatic ring;
$R^{10}$ is a fatty alky(en)yl group;
each group $AO^3$ is independently selected from an alkyleneoxy group, particularly an ethyleneoxy or propyleneoxy group; and
n3 is from 1 to 15, usually 1 to 10, particularly 1 to 5.

The long chain fatty acids in the esters of alkoxylated fatty aliphatic alcohols are desirably $C_8$ to $C_{24}$, especially $C_{10}$ to $C_{18}$, fatty acids. The fatty acids can be straight chain or branched, and saturated or unsaturated, and suitable fatty acids include 2-ethylhexanoic, lauric, myristic, palmitic, stearic, iso-steraric, oleic and linoleic acids. The fatty alcohols used in these esters are desirably $C_8$ to $C_{20}$, especially $C_{10}$ to $C_{18}$. The fatty alcohols may be straight chain or branched, and may be saturated or unsaturated. The fatty alcohols may be selected from alkenyl, or alkynyl groups. Suitable examples include 2-ethylhexyl, lauryl, myristyl, palmityl, palmitoleyl, stearyl, iso-stearyl, oleyl and linoleyl. The alkoxylation will typically be formed of ethyleneoxy or propyleneoxy groups or combinations of ethyleneoxy and propyleneoxy groups, which may form block, tapered block or random chains.

Desirably the alkoxylation is of ethyleneoxy groups or combinations of ethyleneoxy and propyleneoxy groups with more than 50%, usually more than 70%, desirably more than 80%, (molar) ethyleneoxy groups. The number of alkyleneoxy residues is typically from 1 to 100, more usually from 2 to 20, particularly from 3 to 15. In practice this number is an average value and may therefore be non-integral. Examples of suitable esters of long chain fatty acids and alkoxylated fatty aliphatic alcohols include (using INCI nomenclature) PPG-2 myristyl ether propionate (available as Crodamol PMP from Croda Europe) di-PPG-3 ceteth 4 adipate (available as Cromapure GDE from Croda Europe) and di-PPG-2 myreth-10 adipate (available as Cromollient SCE from Croda Europe).

The fatty alkoxylate di- and/or tri-esters of aliphatic and/or aromatic dicarboxylic and/or tricarboxylic acids are typically based on dicarboxylic and/or tricarboxylic acids which are usually $C_1$ to $C_{30}$ acids. The fatty alcohol alkoxylates are typically based on similar types of alcohol to those described above for the esters of long chain fatty acids and alkoxylated fatty aliphatic alcohols and the examples given are equally applicable to these di- and tri-esters. The alkoxylation is also typically similar to that described above for the esters of long chain fatty acids and alkoxylated fatty aliphatic alcohols.

These di- and tri-esters have the advantage that they can provide an exceptional dry emollient feel in topical formulations particularly when compared with other oils of similar molecular weight. The invention accordingly includes an inverse (water in oil) emulsion having a dispersed aqueous phase comprising a solution or dispersion of at least one water soluble polymer, particularly a polymer that forms a viscous solution or dispersion in water, and a continuous oil phase which is or includes an ester oil including an alkoxylated alcohol group, which is a fatty alkoxylate di- and/or W-ester of aliphatic and/or aromatic dicarboxylic and/or tricarboxylic acids.

The esters of fatty carboxylic acids and polyalkoxylates of aromatic alcohols are typically made using the similar types of fatty acid to those described above for the esters of long chain fatty acids and alkoxylated fatty aliphatic alcohols and the examples given are equally applicable to these esters of alkoxylated aromatic alcohols. The aromatic alcohols are typically compounds in which an aromatic group is a substituent on a hydrocarbyl, usually alkyl or alkenyl chain, usually a $C_1$ to $C_{30}$, particularly a $C_1$ to $C_{10}$, chain. Typically the aromatic group includes an aromatic nucleus containing from 6 to 20 carbon atoms (exclusive of substitution), particularly 6, 10 or 14, more particularly 6 or 10, carbon atoms. Examples of suitable aromatic nuclei are benzene ($C_6$), naphthalene ($C_{10}$) and anthracene ($C_{14}$) ring systems. Alkoxylated aromatic alcohols based on these ring systems have one, two or more, but desirably one hydroxyl group(s).

The alkoxylation is again typically similar to that described above for the esters of long chain fatty acids and alkoxylated fatty aliphatic alcohols. Examples of such esters of alkoxylated aromatic alcohols include: PEG-2 PPG-3 cinnamyl linoleate (cis, cis-9,12-octadecanodienoate), PEG-60 PPG-80 cinnamyl laurate, PEG-6 PPG-3 cinnamyl myristate, PPG-5 cinnamyl palmitate, PPG-2 benzyl ether myristate (available as Crodamol STS from Croda Europe), PPG-3 benzyl myristate, PPG-10 benzyl propionate, PPG-10 benzyl myristate, PEG-10 benzyl acetate, PEG-20 benzyl stearate, di-(PEG-3, PPG-9)-4,8-di-hydroxyethyl-naphthyl monopalmitate, PPG-4 2-naphthyl caprate, PPG-4 2-naphthyl myristate EMI22.4 PEG-5, PPG-4 2-naphthyl oleate (cis-9-octadecenoate), PEG-5, PPG-4 2-naphthyl linoleate (cis, cis-9,12-octadecadienoate), PEG-3, PPG-5 2-naphthyl laurate, PEG-3, PPG-5 2-naphthyl behenate, di-(PEG-3)-2,6-di-hydroxymethyl-naphthyl dimyristate, di-(PEG-3)-2,7-di-hydroxymethyl-naphthyl dimyristate and PEG-3, PPG-5 4-naphthyl behenate.

Other emollient and/or non-emollient oils may be included in the inverse emulsions. Examples of such other emollient oils include ester oils, particularly esters of carboxylic acids and aliphatic alcohols more particularly esters of fatty acids and alcohols and carboxylic esters of fatty alcohols including fatty alcohol esters of fatty carboxylic acids; alkoxylate oils particularly polyalkoxylate, especially wholly or mainly polypropyleneoxy, ethers of fatty alcohols e.g. stearyl alcohol 15-propoxylate (Arlamol E ex Croda); medium chain length, particularly branched paraffins such as iso-decane.

Non-emollient oils, particularly hydrocarbon, particularly mineral paraffin, especially iso-paraffin, oils, may be used as or in the continuous phase in inverse emulsion polymerisation. These oils may be retained in the inverse emulsion product or they may be wholly or partially removed e.g. by distillation.

The oil phase will usually comprise from 15 to 70 wt. %, more usually 25 to 50 wt. % and correspondingly the aqueous phase typically comprises 85 to 30 wt. %, more usually 75 to 50 wt. %, of the inverse emulsion. The weight ratio of aqueous phase to oil phase is typically from 0.5:1 to 3:1, usually about 2:1.

The oil phase will usually comprise the oil and oil soluble surfactant, particularly to aid emulsification of the aqueous phase in the oil phase.

Of the oil, the ester oil including an alkoxylated alcohol group will typically comprise from 1 to 100 wt. %, more usually 20 to 60 wt. %, particularly 30 to 55 wt. % of the total oil in the inverse emulsion. When included, the other emollient oil(s) such as normal esters will typically comprise from 1 to 99 wt. %, more usually 40 to 80 wt. %, particularly 45 to 80 wt. % of the oil. When included, any non-emollient oil(s) present will typically comprise not more than 80 wt. %, usually from 5 to 70 wt. %, more usually 20 to 65 wt. %, particularly 40 to 60 wt. % of the total oil in the inverse emulsion. Mixed oil composition s having lower amounts of non-emollient oil(s) may be obtained by distilling the non-emollient oil from the inverse emulsion to give a desired level.

The composition of the final formulation (inverse emulsion polymer dispersion) is typically (by weight %):

|  | Usually | More Usually |
|---|---|---|
| Oil phase | 15 to 70 | 25 to 50 |
| Aqueous phase/active polymer | 85 to 30 | 75 to 50 |
| Of the oil phase: |  |  |
| surfactants | 8 to 25 | 10 to 20 |
| emollient oil | 92 to 75 | 90 to 80 |

The water soluble polymer incorporated in the aqueous phase of the inverse emulsions of the invention may be ionic or non-ionic but is typically based on (meth)acrylic monomers especially hydrophilic acrylic monomers such as (meth)acrylic acid, (meth)acryamide, and (meth)acrylic esters having hydrophilic substitution e.g. one or more hydroxyl groups as in 2-hydroxyethyl (meth)-acrylate. Particularly useful polymers and copolymers can be made using mainly (meth)acrylic acid, especially mainly acrylic acid. Other monomers may be included to provide particular effects (see further below)

In addition to the primary (meth)acrylic monomers, the polymers may include other monomers which provide additional functionality. In particular monomers which include strong acid groups may be included to improve the hard water tolerance and/or the pH range over which the (co-)polymers provide useful thickening or rheology modifying effects. The monomers including strong acid generally include sulphate acid or sulphonic acid groups (or their salts), although phosphate or phosphonate groups (or their salts) may also be used. Examples of such monomers include 2-acrylamido-2-methylpropane sulphonic acid (AMPS), (meth)acrylic acid isethionate, vinyl sulphonic acid and sodium vinyl sulphonate. The proportion of such strong acid containing monomers is typically up to about 90 mol. %, more usually from 5 to 50 mol. %, particularly 10 to 40 mol. %, and desirably 10 to 20 mol. %, of the total monomer used in the water soluble (co-)polymer.

The water soluble polymers are generally at least partially crosslinked e.g. slightly crosslinked, lightly crosslinked etc.) to increase their molecular weight and their capacity to form structure in aqueous solutions. The crosslinking may also provide specific rheology control in aqueous systems. This is typically done by including a minor proportion of a monomer with at least two ethyleneic double bonds. Typically the monomer has just two ethyleneic double bonds. Suitable monomers include diethylenically unsaturated compounds such as methylene bis acrylamide, ethylene glycol di(meth)acrylate, di(meth)acrylamide, vinyloxyethyl acrylate or methacrylate. Crosslinking may also be carried out by including mono-ethylenically unsaturated compounds with other reactivity such as N-(hydroxymethyl)acrylamide before. The amount of cross linking agent used is typically in from 0.01 to 1 mol. % more usually 0.005 to 0.2 mol %, particularly 0.0075 to 0.02 mol %.

Water soluble (co)polymers are commonly used in end product, particularly personal care, formulations to thicken and for rheology modification of the formulation. Thickening involves increasing the viscosity of the product and is used both to give a desired viscosity, which may have sensory and aesthetic benefits, in the product and to assist in stabilising the product, particularly increasing the stability of emulsion and/or dispersion discontinuous phase components. Rheology modification involves changing the flow properties of the product going beyond just increasing the viscosity, in particular it is likely to involve generating non-Newtonian flow properties in the product, commonly shear thinning.

Typically the water soluble polymers will have a molecular weight of at least about 3 kD, more usually at least about 20 kD, particularly more than about 100 kD and especially more than about 1 MD. Typically the maximum molecular weight is about 10, particularly about 4, MD.

To provide stability the inverse emulsions will include water in oil emulsifiers, which are usually relatively hydrophobic, oil soluble surfactants, generally having a Hydrophile Lipophile Balance (HLB) value of no more than about 9, more usually from 2 to 7, particularly from 3 to 5. The water in oil emulsifiers are typically hydrophobic low molecular weight surfactants and/or hydrophobic polymeric surfactants.

Suitable hydrophobic low molecular weight oil soluble surfactants include sorbitan mono, sesqui, and/or tri-fatty, particularly $C_{14}$ to $C_{20}$ mono-unsaturated fatty, especially oleic, acid esters; glycerol mono- and/or di-fatty, particularly $C_{14}$ to $C_{20}$ mono-unsaturated, especially oleic, acid esters; and fatty, particularly $C_{14}$ to $C_{20}$ mono-unsaturated, especially oleic, acid alkanolamides, particularly ethanolamides, especially diethanolamides. Examples of such emulsifiers include sorbitan esters such as sorbitan monooleate ("Span 80" from Croda) and sorbitan isostearate. Such hydrophobic low molecular weight surfactants typically have HLB values in the range 1.5 to 7.5, more usually 2 to 6, e.g. Span 80 has an HLB of 4.3.

In hydrophobic polymeric surfactants, the polymeric hydrophobe typically contains at least 30 carbon atoms, linked to a hydrophile group, typically through a carboxyl function. Examples of suitable polymeric hydrophobe groups include polymeric hydrocarbyl groups, usually having from 50 to 1000, more usually up to 500, carbon atoms and commonly based on olefin polymers such as polyiso-butylene, which may conveniently be linked to the hydrophile through a succinic acid group (typically by an "ene-" reaction between the polymerised olefin and maleic anhydride, to give a hydrocarbyl substituted succinic anhydride that can be further reacted to make the surfactant); and polyester groups, typically a polyester of a hydroxy fatty acid, particularly a hydroxy $C_{12}$ to $C_{20}$ fatty acid such as hydroxy-stearic acid (usually 12-hydroxystearic acid), containing typically from 50 to 200, more usually 100 to 150, carbon atoms, corresponding (where hydroxystearic acid is used to an average of about 7 hydroxystearate residues.

The hydrophile can be a short hydrophile group, particularly derived from an alcohol or polyol, an amine or polyamine, a compound containing both amine and hydroxyl groups, optionally including other groups such as carboxyl groups, or functional derivatives of such amino-, or hydroxyl, or carboxyl groups. Alternatively, the hydrophile group can be a polymeric hydrophile e.g. a polyoxyalkylene group, particularly a polyoxyethylene group. Surfactants having a polyester hydrophobe will usually include a polymeric, particularly polyoxyethylene, hydrophile and surfactants having a hydrocarbyl hydrophobe may have either a short chain or a polymeric hydrophile. Examples of suitable polymeric surfactants include poly(isobutylene) alkanolamides, particularly the ethanolamide, (available as Hypermer 2422 from Croda Europe) and polyethyleneoxy-polyhydroxy-stearate-polyethyleneoxy block copolymers (available as Hypermer B246 from Croda Europe). Such polymeric surfactants are relatively hydrophobic surfactants and typically have HLB values in the range 3 to 8 and particularly 4 to 6, e.g. Hypermer 2422 has an HLB of 4.1.

Mixtures of low molecular weight and polymeric water in oil surfactants may advantageously, and because typically both types are low HLB surfactants usually straightforwardly, be used.

The water in oil emulsifiers are present to stabilise the inverse emulsions. Where the (co-)polymer emulsion is made by inverse emulsion polymerisation, may be included in the emulsion before polymerisation and act to stabilise the inverse emulsion during polymerisation. Where the (co-)polymer is manufactured separately and then dispersed to form the inverse emulsion the water in oil emulsifiers will typically be dissolved or dispersed in the oil prior to inclusion of the (co-)polymer.

The inverse emulsions may include oil in water emulsifiers, particularly as inverting agents i.e. to promote ready and desirably spontaneous inversion (to form oil in water emulsions) on dilution with water. Commonly inverting agents are added after polymerisation of the water soluble polymer (commonly by the manufacturer of the inverse emulsion) before downstream use, particularly after post-polymerisation processing e.g. distillation to remove solvent, but they may be added by a downstream user prior to dilution with or in water.

Typical oil in water emulsifiers (inverting agents) are hydrophilic water soluble emulsifiers usually having a HLB value of at least 7, more usually from 9 to 14. Suitable oil in water emulsifiers include fatty, usually $C_8$ to $C_{18}$, more usually $C_{10}$ to $C_{16}$, alcohol 8 to 20, usually 10 to 12, more usually 11 or 12, polyalkoxylates, particularly polyethoxylates or mixed polyethoxylate/polypropoxylates (usually with a minor proportion of polypropoxylate) such as those sold as Synperonics and Volpos by Croda; and ethoxylated sorbitan esters, particularly mono-oleate, sorbitan esters, such as those sold as Tweens and Crillets by Croda.

The total amount of surfactant included in the inverse emulsions of the invention will typically be from 1 to 20 wt. %, commonly 2.5 to 15 wt. %, more usually from 3 to 10 wt. %, and particularly about 5 to 8 wt. %, of the inverse emulsion. Of this, the water in oil emulsifier (inverter) will typically be from 1 to 10 wt. %, more usually from 2 to 8 wt. %, of the inverse emulsion and typically from 18 to 10 wt. %, more usually from 15 to 12 wt. %, of the polymer inverse emulsion.

The inverse emulsions of the invention may also contain additives which do not adversely affect the final product characteristics such as completing agents, chelating agents/sequesterants e.g. citric acid and EDTA, to prevent metallic impurities having adverse effects, chain transfer agents, to limit/control molecular weight if desired, and solvent, volatile organic solvent, typically used in small amounts to disperse such agents in during polymer synthesis. The total amount of these components it usually not more than 3% wt. % of the total emulsion.

A further benefit that can be obtained is that when certain alkoxylated esters are used they may have or add self emulsifiablity properties to emulsions made using them. In particular addition of further oil(s) may be considerably simplified either to the inverse emulsion or to oil in water emulsions made from them. Typically aqueous dispersions made using mineral oil based inverse emulsions take up to a further 15% wt. % (of the dispersion) of an additional or secondary oil. We have found that aqueous dispersions made inverse emulsions of, or made by the method of the invention, can take substantially larger proportions of secondary oil, typically 35 to 45 wt. %, with the emulsion remaining stable (without additional surfactant) and not causing substantial change in the viscosity of the thickened aqueous system. Surprisingly, we have found that on adding such secondary oil to at least some inverse emulsions of the invention an increase in viscosity is produced. This may be because of improved dispersibility of the rheology modifying polymer, particularly enabling improved space filling and/or chain detanglement.

The inverse emulsions are made by inverse emulsion polymerisation and the process will typically be generally similar to conventional such polymerisations in which monomer(s) are dissolved in water, typically at from 20 to 80 wt. % of total emulsion and, typically also, a crosslinker, together with chain transfer agents, initiators and sequesterants as required.

The aqueous solution is dispersed in the oil phase which includes the hydrophobic component(s), typically including at least one water in oil emulsifier(s) and usually at least one polymeric emulsions stabiliser such as hydrophilically terminated PIBSA derivatives, particularly amides, especially hydroxyl substituted amides such as ethanolamides e.g. Hypermer 2422 (from Croda), and hydrophilic-oleophilic, particularly hydrophilic-oleophilic-hydrophilic block copolymers, especially poly(hydroxy fatty acid); polyethylene oxide; poly(hydroxy fatty acid) triblock copolymers, particularly where the fatty acid is hydroxystearic acid e.g. Hypermer B-246 (from Croda). The mixture is mixed, usually under high shear, to emulsify the aqueous phase in the oil phase and, as necessary deoxygenated. The polymerisation is initiated using an appropriate source of free radicals e.g. thermally or redox generated free radicals or both.

The synthetic reaction system may include chain transfer agents to control the molecular weight and molecular weight distribution of the water soluble polymer. More sophisticated approaches to controlling molecular weight and molecular weight distribution may be used if desired, particularly using controlled free radical polymerisation methods such as Catalytic Chain Transfer (CCT) and Atom Transfer Radical Polymerization (ATRP).

After polymerisation, the inverse emulsion comprises an internal (disperse) phase of the water soluble (co)polymer dissolved in water and an external oil phase. The oil phase used in the polymerisation may be of or include alkoxylated ester or the alkoxylated ester may be added after polymerisation. The polymer content of the emulsion may be adjusted (increased) by distilling (including vacuum and/or steam distilling) solvent from the system. This can be used to reduce the amount of (otherwise inert) water carried with the desired polymer, ultimately possibly to make the emulsion substantially anhydrous. Non-emollient oils that may be desirably absent form the product may be removed at this stage by this distillation.

At this stage it is convenient to add the inverting agent (though it may be added later as is noted above) and it may be desirable to add a polymeric surfactant or wax to act as an oil-phase structurant to improve the shelf-life stability of the inverse emulsion.

The primary application of these inverse emulsions is to provide the water soluble polymers in the personal care products in which they are required. The main effect of including the polymers is to thicken the end products, because the polymer is (in solution) dispersed in an oil phase which is an excellent emollient, with a gain in product attributes from the enhanced emollient performance and/or benefits to product rheology. The inverse emulsions can provide effective thickening in aqueous or mixed aqueous/organic systems typically at concentrations from 0.1 to 10 wt. %, particularly 0.5 to 6 wt. %. The inverse emulsions can provide a combination of thickening/rheology modification with associated emolliency of the alkoxylated esters and possibly other emollient components included in the oil phase.

The inverse emulsions can be used for a wide range of personal care applications. For example, skincare, such as facial moisturisers, hair care, particularly hair styling mousse, hair serums and shampoo, products, sun care, particularly as lotions containing suncare actives, products and cosmetic, particularly skin moisturiser, moisturising foundation and make-up products.

Thus, according to a fourth aspect of the present invention there is provided Personal Care products in the form of an emulsion having an aqueous continuous phase and one or more disperse phases, including an emollient oil phase, which comprise an inverse (water in oil) emulsion of the first aspect, or an inverse (water in oil) emulsion made by a method of the second or third aspect.

Additionally, according to a fifth aspect of the present invention there is provided a method of making a Personal Care emulsion which comprises inverting an inverse (water in oil) emulsion in the presence of water, in particular by diluting the inverse emulsion with or in water, said inverse emulsion being an emulsion of the first aspect or made by the method of either the second or the third aspect.

Examples of typical personal care formulations including the inverse emulsions of the invention as components are outlined below:

Facial Moisturiser

| Component | Function | wt. % |
|---|---|---|
| inverse polymer emulsion | thickener/rheology modifier | 2 |
| steareth-21 | emulsifier | 2 |
| steareth-2 | emulsifier | 2 |
| diisopropyl adipate | emollient | 2 |
| $C_{10-30}$ cholesterol/lanosterol esters | conditioning agent | 5 |
| ethylhexyl palmitate | emollient | 2 |
| propylparaben | preservative | 0.15 |
| deionised water | | to 100 |
| methylparaben | preservative | 0.15 |

Hair Serum

| Component | Function | wt. % |
|---|---|---|
| aqueous sodium laneth-40 maleate/styrene sulfonate copolymer | heat protection | 5 |
| inverse polymer emulsion | thickener/rheology modifier | 3 |
| PPG-3 benzyl ether myristate | glossing agent | 1 |
| diisopropyl adipate | light glossing ester | 1 |
| aqueous cocodimonium hydroxypropyl silk amino acids | smoothing | 1 |
| propylene glycol | humectant | 1 |
| benzyl alcohol + methyl paraben + propylparaben | preservative | 0.2 |
| deionised water | | to 100 |

The use in formulating products, particularly personal care products, of inverse emulsions of water soluble polymers in emollient oils including alkoxylated esters, provides the end product formulator with a multi-functional product. This simplifies the task of the formulator in including improved product aesthetics, particularly rheology, and functionality, particularly emulsification and suspension properties and as noted above in some cases self emulsification. Their use further enables end-users to move away from petrochemically derived oils such as mineral oils e.g. isoparaffins/MOs in support of improving sustainability.

In addition to the above comments, oil can be added to the emulsions after polymerisation. The inclusion or incorporation of alkoxylated ester oils during the polymerisation seems to improve the ease with which this can be done.

Typically, oil additions can be of from 5 to as high as 40% and possible oils which can be added include isoparaffins, other emollient esters, particularly alkoxylated alcohol esters, and silicone oils, particularly dimethicone oils. The exemplar formulation below is challenging with respect to the rheology modifier. Normally, further surfactant would be required in order to stabilise such a high oil phase formulation, however, the inverse emulsion of this invention allows uptake of the secondary oils without the need for additional surfactants and, without negative impact on rheology performance.

The exemplar formulations above use levels of the inverse emulsion of 2 to 3 wt. % of the overall formulation. Higher levels of inverse emulsion may be used, particularly by post formulation addition e.g. to give a total of 5 wt. % or even more e.g. up to 10 wt. %, to obtain higher gel strength or to compensate for formulation additives that tend to reduce the viscosity of break a desired gel. Post addition of this type enables both process optimisation for polymerisation and optimisation of the inverse emulsion to suit the downstream products.

The following Examples illustrate the invention. All parts and percentages are by weight unless otherwise specified.

Materials
Monomers

| AA | acrylic acid |
|---|---|
| AMPS | 2-acrylamido-2methyl-1-propane sulphonic acid |
| MBA | methylene-bis acrylamide |

Oils—Alkoxylated Esters

| AOil1 | PPG-3 benzyl ether myristate |
|---|---|
| AOil2 | Di-PPG-3 Myristyl Ether Adipate |

Oils—Esters

| EOil1 | ethylhexyl cocoate |
|---|---|
| EOil2 | isotridecyl isononanoate |

Oils—Other Oils

| HOil1 | hydrocarbon solvent (low aromatic) |
|---|---|

Surfactants—Polymerisation Stabilisers

| Surf1 | sorbitan oleate |
|---|---|
| Surf2 | Hypermer 2422 |
| Surf3 | Hypermer 2524 |

Surfactants—Inverter Surfactant

| Inv 1 | tridecanol 6-ethoxylate |
|---|---|

Polymerisation Iniators

| ABDV | 2,2'-azobis(4-methoxy-2,4-dimethyl valeronitrile) in dichloromethane ex Waco |
|---|---|
| TBPO | t-butyl peroxide |

Other

| NaOH | aqueous NaOH solution with the w/v concentration in brackets |
|---|---|

SYNTHESIS EXAMPLES

Example SE1

This Example illustrates the manufacture of an inverse emulsion including a lightly cross-linked copolymer of acrylic acid and AMPS as a thickener in the aqueous disperse phase. Aqueous and oil phases were made up by separately mixing the components listed below. In making up the aqueous phase the temperature was kept at less than 30° C. during addition of the NaOH solution (partially neutralising the acid monomer).

| Material | Amount (wt. %) | mmol |
|---|---|---|
| Aqueous phase | | |
| AA | 15.68 | 218 |
| 2 AMPS | 5.98 | 30 |
| MBA | 0.024 | 0.19 |
| NaOH (40% w/v) | 19.97 | 200 |
| water | 23.8 | |
| Oil phase | | |
| AOil1 | 9.23 | |
| EOil2 | 9.23 | |
| HOil1 | 10.79 | |
| Surf1 | 1.22 | |
| Surf2 | 1.22 | |
| ABDV | 0.24 | |

The two phases were sparged with nitrogen for 30 minutes in separate flasks, then were mixed in a 500 ml reaction vessel equipped with a nitrogen sparge, stirrer and thermometer, using high shear under a nitrogen atmosphere to form a water in oil emulsion. Solutions of chelating agents [EDTA] (0.019 wt. %) and citric acid (0.019 wt. %) in water (0.48 wt. %) and t-butylperoxide free radical initiator (0.12 wt. %) in ethylhexyl cocoate (0.24 wt. %) were added to the reactor. Polymerisation was started by adding aqueous sodium metabisulphite (0.012 wt. % in 1.7 wt. % water) over 1 hour using a peristaltic pump.

After the reaction exotherm had subsided, the reaction mixture was kept at 40° C. for 2 hours and volatile solvent (including water) removed by vacuum distillation giving a polymer solids content of about 55 wt. % and finally 4 wt. % Inv1 was added.

Example SE1a

Example SE1 was repeated but using a higher level of crosslinker (MBA at 0.048 wt. %) to give a more highly crosslinked product with a higher molecular weight and viscosity build capacity on dilution in water.

Example SE2

Aqueous and oil phases were made up as described in SE1 using the components listed below:

| Material | Amount (wt. %) | mmol |
|---|---|---|
| Aqueous phase | | |
| AA | 21.12 | 293 |
| MBA | 0.031 | 0.24 |
| NaOH (40% w/v) | 24.94 | 624 |
| water | 23.35 | |
| Oil phase | | |
| EOil2 | 15.66 | |
| HOil1 | 9.16 | |
| Surf3 | 1.22 | |
| ABDV | 0.23 | |

The synthetic method was as described in SE1 but using the following amounts:

| | |
|---|---|
| EDTA solution | 0.018 wt. % |
| citric acid | 0.018 wt. % |
| in water | 0.45 wt. % |
| t-butylperoxide | 0.11 wt. % |
| in ethylhexyl cocoate | 0.23 wt. % |
| aqueous sodium metabisulphite | 0.011 wt. % in 1.57 wt. % water |

The reaction mix was worked up as described in SE1 to give a polymer solids content of about 58 wt. % and 3.5 wt. % of AOil1 and ca 6 wt. % of Inv1 were added.

Example SE3

Aqueous and oil phases were made up as described in SE1 using the components listed below:

| Material | Amount (wt. %) |
|---|---|
| Aqueous phase | |
| AA | 27 |
| MBA | 0.015 |
| NaOH (48 wt. % aqueous solution) | 13.5 |
| water | 28 |
| Oil phase | |
| AOil1 | 3.2 |
| Surf1 | 0.51 |
| EOil1 | 11.7 |
| HOil1 | 11.5 |
| Surf2 | 1.95 |
| ABDV | 0.5 |

The synthetic method was as described in SE1 but using the following amounts:

| | |
|---|---|
| EDTA solution | 0.026 wt. % |
| citric acid | 0.013 wt. % |
| in water | 0.5 wt. % |
| t-butylperoxide | 0.034 wt. % |
| sodium formaldehyde sulphoxylate | 0.04 wt. % in 1.8 wt. % water |

The reaction mix was worked up as described in SE1 to give a polymer solids content of about 58 wt. % and ca 6 wt. % of Inv1 was added.

Example SE4

Aqueous and oil phases were made up as described in SE1 using the components listed below:

| Material | Amount (wt. %) |
|---|---|
| Aqueous phase | |
| AA | 27 |
| MBA | 0.015 |
| NaOH (48 wt. % aqueous solution) | 13.5 |
| water | 28 |
| Oil phase | |
| AOil2 | 3.2 |
| Surf1 | 0.51 |
| EOil1 | 11.7 |
| HOil1 | 11.5 |
| Surf2 | 1.95 |
| ABDV | 0.5 |

The synthetic method was as described in SE1 except that the amounts were changed as follows:

| | |
|---|---|
| EDTA solution | 0.026 wt. % |
| citric acid | 0.013 wt. % |
| in water | 0.5 wt. % |
| t-butylperoxide | 0.034 wt. % |
| sodium formaldehyde sulphoxylate | 0.04 wt. % in 1.8 wt. % water |

The reaction mix was worked up as described in SE1 to give a polymer solids content of about 58 wt. % and ca 6 wt. % Inv1.

Examples SE5

Aqueous and oil phases were made up as described in SE1 using the components listed below:

| Material | Amount (wt. %) |
|---|---|
| Aqueous phase | |
| AA | 24.9 |
| MBA | 0.032 |
| NaOH (48 wt. % aqueous solution) | 17.5 |
| water | 26.2 |
| Oil phase | |
| AOil1 | 6.23 |
| Surf1 | 0.125 |
| EOil1 | 8.7 |
| HOil1 | 11.22 |
| Surf2 | 2.24 |
| ABDV | 0.5 |

The synthetic method was as described in SE1 but using the following amounts:

| | |
|---|---|
| EDTA solution | 0.025 wt. % |
| citric acid | 0.013 wt. % |
| in water | 0.5 wt. % |
| t-butylperoxide | 0.032 wt. % |
| sodium formaldehyde sulphoxylate | 0.04 wt. % in 1.7 wt. % water |

The reaction mix was worked up as described in SE1 to give a polymer solids content of about 58% and ca 6 wt % Inv1 was added.

APPLICATION EXAMPLES

Materials

Inverse emulsions made as described in the Synthesis Examples are identified by their SE numbers.
Comparative inverse emulsions:
CIE1 RMA52—inverse acrylic emulsion with mineral oil continuous phase ex SNF SA
Test Methods
1. Long Term Stability (a key requirement in personal care products)—was assessed on aqueous dispersions (AD) and oil emulsions (OE). The aqueous dispersions were made up by adding a measured quantity of inverse emulsion to a measured amount of water (usually to form a 2 wt. % dispersion of the polymer in water) with stirring to form a smooth gel-like dispersion. The oil emulsions used for testing were personal care formulations made up using the inverse emulsions (Formulations 1 to 4 below). Samples of the formulations were subjected to accelerated ageing by storage at 45° C. for 3 months (normally assessed as equivalent to 12 months storage at ambient temperature). The stability of the formulations was assessed visually on samples taken periodically during the test period.
2. Shelf Life Stability—this was assessed on the water in oil inverse emulsions by centrifuging a weighed sample of the inverse emulsion at 4000 rpm (ca 67 Hz) for 20 minutes. The supernatant liquid was decanted, the residual solid was weighed and the solids reported as a percentage of the whole sample mass (the lower the figure the more stable the sample).
3. Inverted Emulsion Rheology—was assessed using a HAAKE Rheostress 600 at ambient temperature, both on 2 wt. % aqueous dispersions and as emulsion formulations (from Formulations 1 to 4).
4. Self Emulsification—was evaluated on emollient containing dispersions from the inverse emulsions by seeing how much further (secondary) oil can be included in the dispersion, without addition of further emulsifier or stabiliser, without either a viscosity drop or phase separation.

Test Formulations
Samples of Test Formulation 1, 2 and 3 were made up as described below. The Samples are identified in the Application Examples as Fx.y (Formulation x; sample y).
Formulation 1
Samples of a thermal smoothing serum (for treating hair, particularly thermally damaged hair) thickened with inverse emulsions of the invention and with mineral oil based inverse emulsion (C1E) were made up as follows:

| Material | Commercial name | Amount (wt. %) |
|---|---|---|
| Water | | 87.8 |
| Hair treatment polymer | MiruStyle XHP | 5 |
| PPG-3 Benzyl Ether Myristate | Crodamol STS | 1 |
| Diisopropyl adipate | Crodamol DA | 1 |
| Inverse emulsion | | 3 |
| Silk amino acid derivative | Crosilkquat | 1 |
| Propylene glycol | | 1 |
| Preservative | Nipaguard MPA | 0.2 |

The inverse emulsion was diluted in the water and stirred until homogeneous; and the remaining ingredients were then added with stirring.
Formulation 2
Samples of a further thermal smoothing serum thickened were made up as follows:

| | Material | Commercial name | Amount (wt. %) |
|---|---|---|---|
| A | Water | | 87.8 |
| | Hair treatment polymer | MiruStyle XHP | 5 |
| | Aqueous silk amino acids | Crosilk Liquid | 1 |
| | Propylene glycol | | 1 |
| B | Inverse Emulsion | | 3 |
| C | Preservative | Nipaguard MPA | 0.2 |
| | | Crodamol STS | 1 |
| | | Crodamol DA | 1 |

The A components were mixed and stirred until homogeneous; the inverse emulsion B was added with stirring; and the components C were then added with stirring.
Formulation 3
Samples of a facial moisturiser thickened with inverse emulsions of the invention and with mineral oil based inverse emulsion (C1E) were made up as follows:

| | Material | Commercial name | Amount (wt. %) |
|---|---|---|---|
| A | Emulsifier (Steareth-21) | Brij S721 | 2 |
| | Emulsifier (Steareth-2) | Brij S2 | 2 |
| | Diisopropyl adipate | Crodamol DA | 2 |
| | Cholesterol/lanosterol esters | Super Sterol Ester | 5 |
| | 2-Ethylhexyl palmitate | Crodamol OP | 2 |
| | Preservative | propylparaben | 0.15 |
| B | Inverse Emulsion | | 2 |
| C | Water | | 84.7 |
| | Preservative | propylparaben | 0.15 |

The oil phase A components were mixed, heated to 65 to 70° C. and stirred until homogeneous; the inverse emulsion B was added with stirring; the water phase components C were separately mixed, heated to 65 to 70° C. and stirred until homogeneous; the combined mix of components A and B was mixed with the water phase component mix C—for samples F3.1 and F3.3 the water phase was added to the oil phase with stirring and for sample F3.5 the oil phase was added to the water phase with stirring; and the overall mixture allowed to cool to ambient temperature with stirring.
Formulation 4
Samples of a facial moisturiser similar to Formulation 3 were made up using post addition of the thickener as follows:

| | Material | Commercial name | Amount (wt. %) |
|---|---|---|---|
| A | Emulsifier | Brij S721 | 2 |
| | Emulsifier | Brij S2 | 2 |
| | Diisopropyl adipate | Crodamol DA | 2 |
| | Cholesterol/lanosterol esters | Super Sterol Ester | 5 |
| | 2-Ethylhexyl palmitate | Crodamol OP | 2 |
| | Preservative | propylparaben | 0.15 |
| B | Water | | 84.7 |
| | Preservative | methylparaben | 0.15 |
| C | Inverse Emulsion | | 2 |

The oil phase A components were mixed, heated to 65 to 70° C. and stirred until homogeneous; the water phase components B were separately mixed, heated to 65 to 70° C. and stirred until homogeneous; the oil phase was added to the water phase with stirring; the inverse emulsion was added with stirring; and the overall mixture allowed to cool to ambient temperature with stirring.

Application Example AE1

Samples of Formulations 1, 2, 3 and 4 (all OE samples) were subjected to Long Term Stability testing as described above and the results are set out in Table AE1 below.

TABLE AE1

| | | Inverse Emulsion | | |
|---|---|---|---|---|
| Ex. No. | Sample No. | Type | Amount (wt. %) | Stability Result |
| AE1C.1 | F1.1 | CIE1 | 3 | stable |
| AE1.2 | F1.3 | SE1a | 3 | stable |
| AE1C.2 | F2.3 | CIE1 | 3 | stable |
| AE1.4 | F2.1 | SE1a | 3 | stable |
| AE1C.3 | F3.1 | CIE1 | 2 | stable |
| AE1.7 | F3.2 | SE1a | 2 | stable |
| AE1.8 | F3.3 | SE1a | 2 | stable |
| AE1C.4 | F4.1 | CIE1 | 2 | stable |
| AE1.9 | F4.2 | SE1a | 2 | stable |

Application Example AE2

The rheology of the polymer inverse emulsions of Example SE1 and SE1a after forming an aqueous dispersion (AD) by inversion on dilution with water to give a 2 wt. % copolymer concentration in the dispersion and after formulating the polymer in an oil in water emulsion formulation (OE) (Formulation 3 above) was assessed by the general method described above. These data were compared with results obtained using a conventional commercially available (mineral oil based) inverse emulsion polymer.

TABLE AE2

| | | Yield point (Pa) | | Z-shear visc. (mPas) | | Visc. (Pas) | |
|---|---|---|---|---|---|---|---|
| Ex. No. | Polymer | AD | OE | AD | OE | AD | OE |
| AE2.1 | SE1 | 52.6 | 76.3 | 17.0 | 32.0 | 59 | 180 |
| AE2.2 | SE1a | 70.5 | 110.5 | 29.6 | 106.9 | 78.8 | 300 |
| AE2C.1 | CIE1 | 32.7 | 89.7 | 14.6 | 66.0 | 36.4 | 177 |

The aqueous dispersions are shear thinning, indicated by the substantial viscosity decrease under shear. The dispersions show a pattern for yield point, zero shear viscosity and Brookfield viscosity in that the dispersions using the copolymer of SE1a give the highest values with the conventional copolymer the lowest values. One contributor to this pattern is likely to be that the higher level of crosslinker used in SE1a gives a copolymer with higher molecular weight.

The emulsions made from the aqueous dispersions obtained by inverting the inverse co-polymer emulsions, show shear thinning, with signs of thixotropy at the highest shear values. Slippage was observed for all of the emulsions at high shear stress. The trend between the sample differed from that of the dispersions in that the copolymer of SE1a gave the highest yield stress and zero shear viscosity, but that of the copolymer of SE1 was somewhat lower than that of the conventional copolymer with the Brookfield viscosities of these two polymers being similar.

Application Example AE3

The stability of the emulsions was assessed as described above. The results, which show a substantial improvement in emulsion stability for the inverse emulsions of the invention, are set out in Table AE3 below:

TABLE AE3

| Ex. No. | Inverse Emulsion | Residue(wt. %) |
|---|---|---|
| AE3C.C | CIE1 | 37 |
| AE3.1 | SE2 | 8 |

Application Example AE4

This Example illustrates the inclusion of additional or secondary oil to diluted inverted emulsions. Dilute emulsions were made up at 2 wt. % thickening polymer on water. Secondary oil was added in stages and the Brookfield viscosity being measured until the emulsion became unstable. Three inverse emulsions were tested, one using mineral oil CIE1, one using the direct polymerisation emulsion of SE2 (EOil 1 without any alkoxylated ester oil) designated SE2' and the inverse emulsion of SE2 (using a combination of EOil1 and AOil1). The results are set out in Table AE4 below and show that inverse emulsions of the invention can tolerate secondary oil significantly better than either mineral oil or conventional ester oils. The increase in viscosity noted above is also shown by these data.

TABLE AE4

| Ex. No. | Inverse Emulsion | Oil | Sec. Oil (wt. %) | Visc. (%) |
|---|---|---|---|---|
| AE4C.1 | CIE1 | Mineral oil | 0 | 100 |
| | | | 3.3 | 83 |
| | | | 6.4 | 79 |
| | | | 9.25 | 71 |
| | | | 12* | 49 |
| AE4C.2 | SE2' | EOil3 | 0 | 100 |
| | | | 9.1 | 97 |
| | | | 16.67 | 103 |
| | | | 23.1 | 106 |
| | | | 28.5 | 108 |
| | | | 32.5* | 114 |
| AE4.1 | SE2 | EOil3 + AOil1 | 0 | 100 |
| | | | 6.25 | 98 |
| | | | 11.75 | 103 |
| | | | 16.67 | 102 |
| | | | 25 | 110 |
| | | | 31.8 | 117 |
| | | | 37.5 | 119 |
| | | | 40* | 122 |

*limit of stability on addition of secondary oil

Application Example AE5

The properties of inverse emulsion polymers was evaluated using 2 wt. % aqueous polymer solutions made by inverting samples of inverse emulsion polymers, in panel tests to detect sensorial differences between products. The samples used were made up using mineral oil based inverse emulsion CIE1 and one made with the inverse emulsion of SE2. Two panels were used:

A triangle panel test in which 15 panellists were presented with 3 samples (identified only by codes). Panellists were told that two samples were the same and one different. Skinfeel was evaluated and the panellists asked to identify the sample which felt different. In the test, 11 out of 15 panellists correctly identified the 'different' sample.

A separate panel of 12 people were subsequently asked to carry out a preference test between dispersions containing the inverse emulsion of SE2 and a one containing CIE1 by indicating whether and what preference they had between the two; considering attributes such as skin feel, absorption, rub-in time and pick-up. The majority of panellists preferred the emollient-containing LDP over mineral oil.

Application Example AE6

A Body Butter formulation including 30 wt. % oil was made up with an inverse emulsion of the invention using the following formulation:

|   | Material | Commercial name | Amount (wt. %) |
|---|---|---|---|
| A | Triethylhexanoin | Crodamol GTEH | 4 |
|   | Diisopropyl Adipate | Crodamol DA | 2 |
|   | Myristyl Lactate | Crodamol ML | 3 |
|   | isostearyl isostearate | Crodamol ISIS | 5 |
|   | Cocoa butter |  | 7 |
|   | *Theobroma Grandiflorum* oil | Crodamazon Cupuacu | 3 |
|   | Avocado Oil (including unsaponifiables) | Avocadin | 2 |
|   | PPG-3 Benzyl Ether Myristate | Crodamol STS | 4 |
| B | Water |  | 63 |
|   | glycerine | Pricerine 9091 | 4 |
|   | Inverse Emulsion of SE2 |  | 2 |
| C | Preservative | Euxyl K300 | 1 |

The emollient oil components A and the aqueous based components B were separately mixed with stirring and then combined with stirring, after which component C was stirred in.

This formulation illustrates substantial addition of secondary oil to produce a thickened personal care product having an overall 30 wt. % oil content.

It is to be understood that the invention is not to be limited to the details of the above embodiments, which are described by way of example only. Many variations are possible. All of the features described herein may be combined with any of the above aspects, in any combination.

The invention claimed is:

1. An inverse (water in oil) emulsion made by inverse emulsion polymerisation, comprising:
   i) a disperse aqueous phase comprising a solution or dispersion of at least one water soluble polymer that forms a viscous solution or dispersion in water; and
   ii) 25 to 50 wt. % of a continuous oil phase, relative to the total weight of the inverse emulsion, wherein:
      a) the continuous oil phase comprises an ester oil having an alkoxylated alcohol group, wherein the alkoxylated ester is selected from one or more of the following compounds either alone or in any combination:
         1) esters of long chain fatty acids and alkoxylated fatty aliphatic alcohols of formula (I):

$$R^1-C(O)O(AO^1)_{n1}R^2 \quad (I)$$

wherein:
   $R^1$ represents a $C_7$ to $C_{23}$ hydrocarbyl;
   $AO^1$ group independently represents an alkyleneoxy group;
   n1 represents a value from 1 to 15;
   $R^2$ represents a fatty aliphatic group;

ii) diesters and/or triesters of aliphatic and/or aromatic dicarboxylic and/or tricarboxylic acids and fatty alkoxylated alcohols of the formula (II):

$$(R^5)_m-R^3-[C(O)O(AO^2)_{n2}R^4]_2 \quad (II)$$

wherein:
   $R^3$ represents a $C_2$ to $C_{10}$ hydrocarbyl group;
   $R^4$ represents a fatty hydrocarbyl group;
   $AO^2$ group represents an alkyleneoxy group;
   n2 represents a value from 1 to 15;
   $R^5$ represents a group of formula $R^6O(O)C-$, wherein $R^6$ is selected from H, a salt forming moiety comprising an alkali metal or an amine, or an $(AO^2)_{n2}R^2$ group, wherein $-AO^2$, n2 and $R^2$ are as defined above; and
   m represents a value equal to either 0 or 1;
   iii) esters of fatty carboxylic acids and polyalkoxylates of aromatic alcohols of formula (III):

$$R^9O-(AO^3)_{n3}-C(O)-R^{10} \quad (III)$$

wherein:
   $R^9$ represents a group comprising an aromatic ring;
   $R^{10}$ represents a fatty alkyl group or a fatty alkenyl group;
   $AO^3$ group independently represents an alkyleneoxy group; and
   n3 represents a value from 1 to 15; and
   b) the ester oil comprises 30 to 55 wt. % of the total oil in the emulsion.

2. An inverse (water in oil) emulsion made by inverse emulsion polymerisation, comprising:
   i) a disperse aqueous phase comprising a solution or dispersion of at least one water soluble polymer that forms a viscous solution or dispersion in water; and
   ii) 25 to 50 wt. % of a continuous oil phase, relative to the total weight of the inverse emulsion, wherein the continuous oil phase comprises an ester oil having an alkoxylated alcohol group, wherein the alkoxylated ester is one or more compound of formulae (IIa) or (IIb), or a combination thereof:

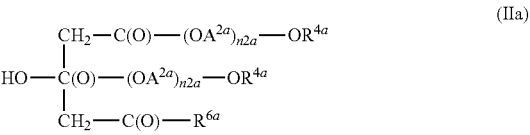

(IIa)

wherein:
$R^{4a}$ independently represents a fatty hydrocarbyl group;
$OA^{2a}$ group independently represents an alkyleneoxy group;
n2a independently represents a value from 1 to 15; and
$R^{6a}$ represents an H or an $(AO^{2a})_{n2a}R^{2a}$ group, wherein the $R^{2a}$ independently represents a fatty aliphatic group;

$$R^{4b}(OA^{2b})_{n2b}O(O)C.CHR^7-CHR^7.C(O)-(OA^{2b})_{n2b}-OR^{4b} \quad (IIb)$$

wherein:
$R^{4b}$ independently represents a fatty hydrocarbyl group;
$OA^{2b}$ group independently represents an alkyleneoxy group;
n2b independently represents is from 1 to 15; and $R^7$ independently represents a H, $C_1$ to $C_{30}$ alkyl, or $C_2$ to $C_{30}$ alkenyl group, or together the two $R^7$ groups represent a direct bond between the carbon atoms to which they are attached.

3. A Personal Care product in the form of an emulsion having an aqueous continuous phase and one or more disperse phases, including an emollient oil phase, which comprise an inverse (water in oil) emulsion as claimed in claim 1, or an inverse (water in oil) emulsion made by the method comprising:
   a) dispersing in an oil phase an aqueous solution of monomers, said monomers being polymerisable to form a water soluble or dispersible polymer, said oil phase comprising at least one ester oil having an alkoxylated alcohol group; and
   b) polymerising said monomers to form a colloidal suspension of particles, of a solution or dispersion of the resulting polymer in water, in the oil.

4. A Personal Care product in the form of an emulsion having an aqueous continuous phase and one or more disperse phases, including an emollient oil phase, which comprise an inverse (water in oil) emulsion as claimed in claim 2.

* * * * *